United States Patent
Krüger et al.

(10) Patent No.: US 12,252,436 B2
(45) Date of Patent: Mar. 18, 2025

(54) SINGLE-PIECE REACTION VESSEL MADE OF GLASS, PRODUCTION METHOD, AND ANALYSIS METHOD

(71) Applicant: LPKF LASER & ELECTRONICS AG, Garbsen (DE)

(72) Inventors: Robin Krüger, Hannover (DE); Malte Schulz-Ruhtenberg, Wunstorf (DE); Jan Van Aalst, Garbsen (DE); Moritz Woller, Neustadt (DE)

(73) Assignee: LPKF LASER & ELECTRONICS AG, Garbsen (DE)

( * ) Notice: Subject to any disclaimer, the term of this patent is extended or adjusted under 35 U.S.C. 154(b) by 144 days.

(21) Appl. No.: 17/774,961

(22) PCT Filed: Nov. 10, 2020

(86) PCT No.: PCT/EP2020/081585
§ 371 (c)(1),
(2) Date: May 6, 2022

(87) PCT Pub. No.: WO2021/094286
PCT Pub. Date: May 20, 2021

(65) Prior Publication Data
US 2022/0388897 A1    Dec. 8, 2022

(30) Foreign Application Priority Data
Nov. 12, 2019 (DE) .......................... 102019217466.3

(51) Int. Cl.
C03C 15/00 (2006.01)
C03C 23/00 (2006.01)
(Continued)

(52) U.S. Cl.
CPC .......... *C03C 15/00* (2013.01); *C03C 23/0025* (2013.01); *C03C 27/06* (2013.01); *C12M 23/22* (2013.01)

(58) Field of Classification Search
None
See application file for complete search history.

(56) References Cited

U.S. PATENT DOCUMENTS 5,874,362 A * 2/1999 Wong ................ H01L 21/76232
257/E21.549
5,919,607 A    7/1999 Lawandy
(Continued)

FOREIGN PATENT DOCUMENTS

EP    1867612 A1    12/2007
EP    2011857 A1    1/2009
JP    2013197398 A *    9/2013

OTHER PUBLICATIONS

Deutsch et al., "A novel miniature cell retainer for correlative high-content analysis of individual untethered non-adherent cells", Lab Chip, 2006, pp. 995-1000, vol. 6, The Royal Society of Chemistry.
(Continued)

*Primary Examiner* — Shamim Ahmed
(74) *Attorney, Agent, or Firm* — Greer, Burns & Crain, Ltd.; Steven P. Fallon

(57) ABSTRACT

A method of production of glass reaction vessels includes irradiating a laser beam of a wavelength for which a first glass plate is transparent onto the surface of the first glass plate. The first hiss plate is etched. Etching of the first glass plate is terminated when the recesses extend, over only a portion of the thickness of the first glass plate and therefore the recesses have a bottom formed in the first glass plate as a single piece.

7 Claims, 2 Drawing Sheets

Figure 1:
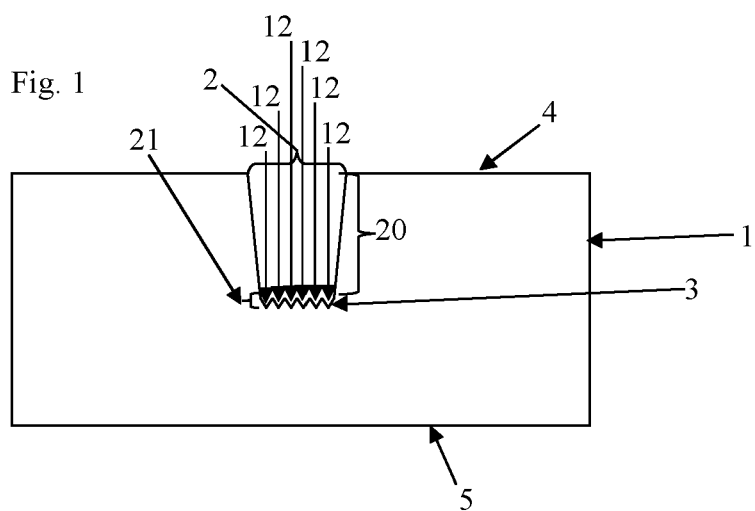

(51) Int. Cl.
    *C03C 27/06*    (2006.01)
    *C12M 1/00*    (2006.01)

(56) References Cited

U.S. PATENT DOCUMENTS

| | | | |
|---|---|---|---|
| 9,832,882 B2* | 11/2017 | Chung | H05K 3/1258 |
| 9,924,601 B2* | 3/2018 | Ostholt | C23C 18/31 |
| 2003/0211014 A1 | 11/2003 | Jacquorie et al. | |
| 2009/0013724 A1 | 1/2009 | Koyo et al. | |
| 2009/0261082 A1 | 10/2009 | Wagner | |
| 2010/0050692 A1 | 3/2010 | Logunov et al. | |
| 2013/0029875 A1 | 1/2013 | Stehno-Bittel et al. | |

OTHER PUBLICATIONS

International Search Report and Written Opinion from the corresponding International Patent Application No. PCT/EP2020/081585, dated Jan. 29, 2021.

* cited by examiner

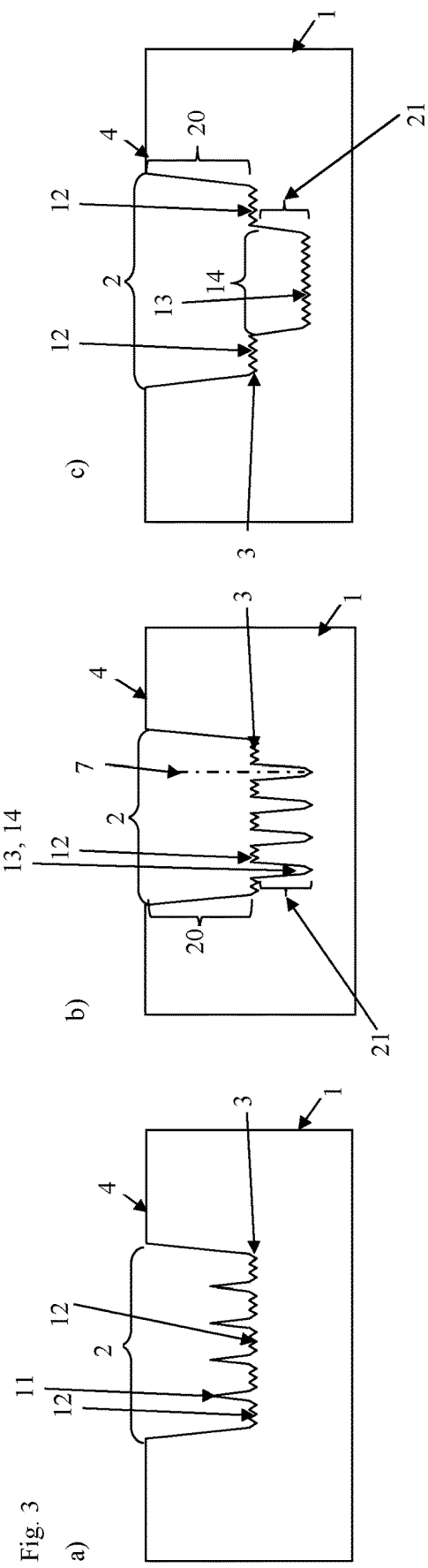

SINGLE-PIECE REACTION VESSEL MADE OF GLASS, PRODUCTION METHOD, AND ANALYSIS METHOD

The present invention relates to a method of producing reaction vessels of glass formed in the form of recesses in glass. The glass in which the reaction vessels are formed in an arrangement is single-piece, such that the reaction vessels are formed in one-piece glass, particularly in a glass plate. The method produces an arrangement of a plurality of reaction vessels formed in single-piece glass, e.g., an arrangement of 25×25 fields of 8×12 reaction vessels each. The reaction vessels are formed in a plurality in a one-piece glass plate consisting of a first glass plate.

The process has the advantage of forming recesses without mechanical impact on a solid glass, forming reaction vessels which therefore have no mechanical damages, e.g. no microcracks. The reaction vessels have a large aspect ratio of depth to diameter. Another advantage is that the process for producing the reaction vessels can proceed at least without selectively coating the glass surface in which the cross-sectional openings of the reaction vessels are formed, optionally without any coating of the glass surfaces in which the reaction vessels are formed.

STATE OF THE ART

Deutsch et al, Lab Chip, 2006, 69, 995-1000, describe the production of reaction vessels of a diameter of 20 µm at 8 µm depth in a glass plate by etching after applying a mask of chromium and photoresist thereon.

US 2003/0211014 A1 describes the production of reaction vessels in glass by means of a tool to which ultrasound is applied, and abrasives between the tool and the glass.

EP 1 867 612 A1 describes microtiter plates with 96 wells made of a bottom of glass that is transmissible for UV and connected by glass frit to a glass plate in which continuous recesses form the side walls of the wells.

EP 2 011 857 A1 describes the generation of surface structures on the bottom of microtiter plates by means of a photolithographic process.

OBJECT OF THE INVENTION

The invention has the object of providing an alternative production method which is particularly suitable for producing reaction vessels with a large aspect ratio at an overall small volume in glass, as well as providing an arrangement of a plurality of such reaction vessels in glass. Preferably, the method shall be suitable to provide an arrangement of such reaction vessels in which arrangement the glass forms a high optical contrast to cells in the reaction vessels under irradiation with light.

DESCRIPTION OF THE INVENTION

The invention achieves the object by the features of the claims and, in particular, by a method for producing reaction vessels of glass and by the reaction vessels made of glass obtainable by the method. The method comprises or consists of the steps of 1. irradiating, preferably point-like and further preferably perpendicularly irradiating a laser beam of a wavelength for which a glass plate is transparent, onto the locations of the surface of the glass plate at which a recess each is to be produced as a reaction vessel, wherein the laser beam preferably consists of laser pulses, e.g. with pulse lengths of at most 100 µs, and the focus position of the laser pulses is adjusted such that their focus, in particular in the direction of the propagation direction of the laser irradiation, does not extend over the entire thickness of the glass plate, and that the first glass plate is irradiated with laser pulses at the locations at which a recess is to be produced at a plurality of positions spaced apart from one another,
2. etching the glass plate, preferably for a time sufficient to produce recesses of a depth, preferably of at least 40 µm or at least 30 µm, preferably with an aspect ratio of at least 2, at least 4, at least 5, or at least 6 of depth to diameter that is measured in the plane of the first surface, along the locations to produce the recesses, wherein the etching of the glass plate is terminated when the recesses extend only over a portion of the thickness of the first glass plate, and therefore the recesses have a bottom formed in a single piece in the first glass plate, such that preferably the bottoms of the recesses forming the reaction vessels have a recess at each position to which a laser pulse has been irradiated or are formed by recesses at each position to which a laser pulse has been irradiated.

Adjusting the focus position of the laser pulses in such a way that their focus, in particular in the direction of the propagation direction of the laser irradiation, does not extend over the entire thickness of the glass plate can be achieved by adjusting the focus position of the laser pulses in such a way that their focus, in particular in the direction of the propagation direction of the laser irradiation, extends only over a portion of the thickness of the glass plate, e.g. over a first thickness section of the glass plate.

Each glass plate herein can be an object made of glass with a lateral extent greater than its thickness. Glass plates can thus have a rectangular, round or otherwise shaped perimeter that delimits their opposite surfaces.

The reaction vessels are formed by recesses in a glass plate, the recesses having exactly one opening lying in the plane of a first surface of the glass plate. Uses of the reaction vessels are not limited to chemical reactions, but include biochemical, biological and physical processes. These can be processes involving single cells, which can be animal or plant cells or yeast cells, bacteria, viruses, proteins, etc., or clusters of these.

The punctiform irradiation is achieved by focusing the laser irradiation onto a point having a size of a few micrometers, e.g. 1 to 10 µm or up to 5 µm. Therein, it is advantageous when the focus of the laser irradiation extends over a length along the direction of propagation of the laser beam that is substantially greater than the Rayleigh length of a corresponding laser beam of a Gaussian profile. This can be achieved by suitable optical devices, e.g. diffractive optical elements. Irradiating may be an irradiating that does not pass through the glass plate, but is performed less deeply into a first thickness portion of the first glass plate adjacent to the first surface, e.g. in that the focus of the laser irradiation in the direction of the propagation direction of the laser irradiation does not extend over the entire thickness of the glass plate, but the laser irradiation extends from a first surface of the glass plate only into a first thickness section adjacent to the first surface and ends in the first thickness section, so that the laser irradiation does not extend into an adjacent second thickness section of the glass plate. Since an interaction between the laser irradiation and the material of the glass plate occurs only at the focus, it is thus possible to have the interaction region end within a first thickness section of the glass plate. Preferably, the laser irradiation consists of laser pulses.

The first surface of the first glass plate, as well as the second surface opposite to it in the absence of a coating of etch resist, is removed significantly faster than the neighboring areas during etching at the locations where the laser was irradiated onto the glass plate and where the laser beam exited opposite. Therefore, the areas of the first surface of the glass plate are removed more slowly and uniformly at a distance from the locations of point laser irradiation due to the absence of a coating, e.g., of etching resist. Therefore, except for the recesses, the first surface is formed by surface sections arranged in one plane from which the recesses extend into the glass volume of the glass plate. The surface portions, which are arranged in a common plane and form the first surface from which the recesses are worked off, are formed by the end faces of the walls that lie between the recesses.

Generally optionally, in a process comprising or consisting of the steps, the second surface of the glass plate may be coated throughout with etch resist to prevent the formation of recesses from the second surface into the glass plate or uniform ablation from that surface. According to the invention, the pulsed laser beam is controlled when irradiating so that the intensity is only sufficient to traverse a first portion of the thickness of the first glass plate to modify the glass plate along the light path, e.g., by adjusting the distance of the focal position relative to the first surface of the glass plate. For this purpose, e.g. the focal position of the laser pulses is adjusted such that the laser pulses penetrate the first glass plate only up to a thickness portion.

Optionally, in step 1 the punctiform irradiated laser beams, at which a recess to form a reaction vessel is etched in step 2, are arranged in the plane of the first surface of the glass plate at a distance of at least or exactly the diameter of one of the reaction vessels plus the thickness of a wall between the reaction vessels. The diameter of the reaction vessels is adjustable by the reaction conditions and the duration of the etching, since the etching is concentric about the linear path taken by the irradiated laser beam through the glass plate. The walls located between the reaction vessels terminate in a common plane. The end faces of these walls lie in a common plane and form the first surface or form the first surface in a common plane, the first surface being interrupted by the recesses. Preferably, the first surface is interrupted only by the cross-sections of the recesses.

The laser beam is preferably pulsed at each of the locations where it is irradiated onto the glass plate, e.g., with a wavelength of 1064 nm to 515 nm, preferably with pulse lengths of at maximum 100 ps or at maximum 50 ps, preferably at maximum 10 ps. Generally, the laser is set up so that the laser beam does not hit the glass plate between locations. Preferably, the laser beam is irradiated punctiform and in perpendicular to the surface of the glass plate.

Preferably, this surface onto which the first laser beam has been irradiated forms the first surface of the first glass plate.

Generally, the glass plate is also called the first glass plate.

The etching is carried out, e.g., with hydrofluoric acid, e.g. 1 to 48 wt. %, and/or sulfuric acid and/or hydrochloric acid and/or phosphoric acid and/or nitric acid, or potassium hydroxide solution, at e.g. up to 140° C.

E.g., the glass plate may have a thickness before etching of up to 1000 µm, preferably 100 to 1000 µm, e.g., up to 800 µm, e.g., 300 to 500 µm, and a thickness after etching that is smaller by 50 to 700 µm, e.g., smaller by up to 200 µm.

In step 3, the etching of the glass plate is terminated when the recesses extend over only a portion of the thickness of the glass plate such that the depth of the recesses into the first glass plate is only a portion of the thickness of the glass plate and, therefore, the recesses have a bottom formed in a single piece in the glass plate.

The recesses preferably extend at an angle of, e.g. 0° to 15° tapering conically or frustroconically and extending from the first surface of the glass plate into the volume thereof.

Optionally, in general the glass plate may be subjected to etching without a coating, e.g., without a mask and/or without etch resist, so that the process has the advantage of being performed without applying and without removing etch resist from a glass plate. Generally, at least the first surface of the glass plate remains without etch resist and without mask and is etched without etch resist.

Generally optionally, in particular in a process comprising or consisting of steps 1 to 3, the second surface of the glass plate is completely coated with etch resist so that the etching is performed only from the first surface, or the laser which irradiates the laser beam is arranged such that the laser beam traverses only a portion of the thickness of the glass plate, resp. such that the laser beam terminates within the thickness of the glass plate. In this embodiment, each location of the glass plate at which a recess is to be created is irradiated with laser beams punctiform at a plurality of positions spaced apart from one another, e.g. at least 2 or at least 3 or at least 10 or at least 30 positions, the laser beams preferably being irradiated parallel to one another and perpendicularly to the glass plate, successively or simultaneously. The positions form the location at which the etching removes the glass plate faster than at surface areas remote therefrom. The positions where the laser was irradiated lead to a uniformly fast removal of the glass during etching and together form a recess. The positions that are irradiated in the area of a location and form a location are arranged, e.g., at a distance of 1 to 10 µm. Preferably, the positions are arranged within the area around each location where a recess is to be formed in each case. Preferably, the positions at which laser beams are irradiated around a location or to form a location are arranged at a distance of 1 to 10 µm, e.g. 2 to 5 µm or up to 3 µm, which is determined in particular in the plane of the first surface of the first glass plate.

Generally, a recess can be created by a single laser pulse or multiple laser pulses. In the case of a single laser pulse, the diameter of the recess is determined primarily by the duration of etching. When a recess is created by multiple laser pulses, the diameter of the recess is determined by the number and distance of positions at which laser beams are irradiated for a location and penetrate the first glass plate. The depth of the recess in the volume of the first glass plate can be determined by the duration of etching and because the laser beam penetrates the glass plate only to a portion of the thickness and does not irradiate completely through the glass plate.

Optionally, around each location where a recess is to be formed, a laser beam is irradiated on a circumferentially closed path, which is preferably annular, rectangular or hexagonal, which is formed, e.g., by laser beam pulses irradiated side by side. Therein, laser beam pulses can be irradiated onto the first glass surface along the circumferentially closed path, e.g., at a distance of the laser beam pulses of 3 µm side by side determined on the first surface of the first glass plate. Optionally, therefore, the glass plate may be irradiated with laser beams at each location at a plurality of positions spaced apart from each other, each punctiform, and a laser beam, e.g., formed by laser beam pulses irradiated side by side, may be irradiated around these positions along a circumferentially closed path. The irradiation of a laser beam along a circumferentially closed path has the advantage that, during subsequent etching, recesses are formed with a wall that extends from the first surface and has a cross section that includes the circumferentially closed path.

Therefore, the glass plate may as a single piece have the reaction vessels as recesses. In this embodiment, the bottom of the reaction vessels is formed by the material of the glass plate. Preferably, the bottom of the reaction vessels is formed by a plurality of adjacent recesses arranged side by side approximately in a plane parallel to the first surface and parallel to the plane of the second surface of the glass plate.

In this embodiment, the bottom of the recesses may have microstructures that are arranged for near-field illumination of the interior volume of the recesses. Such microstructures may, e.g., be in the form of narrow, tall glass tips and thus act as optical waveguides for illumination or may be capable of influencing the position or orientation of individual cells or collections of cells. Such structures can be made, e.g., by forming a recess by etching a plurality of positions onto which closely spaced laser pulses have been irradiated. If a single laser pulse is omitted from the center of the recess, a glass tip remains standing here within the recess after the etching process. Generally, a recess can be created in the process by irradiating laser pulses side by side at positions and subsequent etching, wherein the positions are arranged at equal distances from each other of at maximum 10 µm, e.g. 1 to 5 µm or up to 3 µm, and together form a location, wherein at least 2 or at least 3 positions are arranged at a greater distance, e.g. at a distance of 10 to 30 µm, e.g. 15 to 20 µm distance. The at least 2 or 3 positions of the laser pulses arranged at a greater distance between them have, e.g., the area in which a laser pulse is omitted at the same distance, or surround the area in which a glass tip remains standing during etching.

Generally, laser pulses can be irradiated into the glass plate at different depths at positions that form a location where a recess is formed by etching. Laser pulses can e.g. be irradiated deeper into the thickness of the glass plate at positions and penetrate deeper, and other laser pulses can be irradiated less deep into the thickness of the glass plate at positions. During subsequent etching, deeper or further recesses are formed at positions where laser pulses were irradiated deeper into the glass plate, and the bottom of the recess is formed at a lesser depth at positions where laser pulses were irradiated less deeply into the glass plate. Generally, depending on the distance of the positions, a concave recess can be formed in the bottom at each position. A recess having a bottom and further deeper recesses therein can be produced by irradiating laser pulses in the share of the positions that are to form the bottom less deeply into the glass plate and irradiating laser pulses in the share of the positions that are to form further recesses extending from the bottom deeper into the glass plate to deeper into the glass plate, and subsequent etching. For a larger diameter of further recesses extending deeper into the glass plate starting from the bottom of a recess, laser pulses irradiated deeper into the glass plate can be arranged at adjacent positions, e.g. at a distance of 1 to 10 µm, e.g. 2 to 5 or up to 3 µm, so that etching penetrates deeper into the glass plate at these positions. Thus, laser pulses can be irradiated less deeply into the glass plate at a share of the positions, and laser pulses can be irradiated more deeply into the glass plate at the share of the positions, so that etching at the positions where the laser pulses have been irradiated less deeply produces a bottom with concave recesses at a lesser depth, and at the positions where laser pulses have been irradiated more deeply produces further recesses extending more deeply into the glass plate.

In this embodiment for the production of reaction vessels formed in a single-piece glass plate, or of only one glass plate, the etching is carried out for a duration of time sufficient to achieve a desired depth of the recesses in the glass volume of the glass plate, which lies at a distance from the second surface, or is etched only for a duration of time after which the glass plate still has a closed second surface. Optionally, the bottom of the reaction vessels may thereby have concave depressions having a parabolic or conical cross-section. Such concave depressions may be formed at any position where a laser beam has been irradiated punctiform. Preferably, such concave depressions have a cross-sectional opening and a depth of a few micrometers, e.g., 1 to 5 µm. Preferably, the bottom of each recess or reaction vessel has at least 3 concave depressions.

In embodiments in which the second surface of the first glass plate is coated all over with etch resist, etching acts only from the first surface. The coating of the second surface results in the formation of recesses that extend cylindrically or conically from the first surface toward the second surface and prevents etch removal from the second surface, such that the recesses extend only into a portion of the thickness of the glass plate. In this embodiment, etching can generally be allowed to act exclusively on the first surface of the glass plate until the recess extends into the plane of the second surface of the glass plate. It has been found that when the second surface is coated with etch resist, the etching produces recesses in a portion of the thickness of the glass plate the wall of which recesses is perpendicular or at an angle of the cone shape or frustrocone shape to the plane of the second surface.

Generally, the recesses extend perpendicular to the first surface into the glass plate, which for each of the recesses forms a thickness portion opposite to the first surface as a-single-piece bottom.

The reaction vessels have e.g. a depth of at least 40 µm, at least 50 µm or at least 100 µm or at least 150 µm, e.g. up to 250 µm or up to 200 µm. The reaction vessels have, e.g., a diameter of at least 10 µm or at least 30 µm, e.g. up to 200 µm or up to 1 mm, generally preferably with an aspect ratio of depth to diameter of at least 2, at least 4, at least 5 or at least 6. The recesses of the first glass plate have, e.g., an internal volume within the first glass plate of from 1 µL to 1 µL.

The recesses formed in the glass plate may have a larger cross-section in an upper thickness section 20 adjacent to the first surface than in a lower thickness section 21 adjacent thereto, which is divided into at least two partial recesses. Between the partial recesses extending over the lower thickness section 21, optionally partial walls 22 are formed as a single piece from the glass sheet over the lower thickness section 21. These partial walls 22 are spaced from each other around the partial recesses. These partial walls 22 are formed by irradiating laser pulses that penetrate only maximally into the upper thickness section 20 of the glass plate in the region of the partial walls 22, and irradiating laser pulses that penetrate deeper into the glass plate in the region of the partial recesses, and subsequent etching of the glass plate. During etching, a recess 2 forms in the upper thickness portion 20 adjacent to the first surface 4 of the glass plate which recess extends over the area of at least two partial recesses 2'. The longitudinal center axes 7 of the partial recesses 2' may be arranged, e.g., at a distance of 10 to 100 µm. The partial walls 22 extend over the lower thickness section between the partial recesses 2', wherein the partial recesses 2' may have a diameter of, e.g., 1 to 50 in the plane of the second surface of the glass plate 1. The upper thickness section 20 herein is also referred to as the first thickness section, and the lower thickness section 21 is also referred to as the second thickness section. The upper thickness section 20 and the lower thickness section 21 extend, starting from the first surface 4 of the glass plate 1, independently of each other, e.g., up to at least 20% or at least 30% or at least 40 or at least 50%, e.g., up to 80% or up to 70% or up to 60% of the thickness of the original glass plate 1. Therein, the lower thickness section 21 extends to a smaller or to a greater extent into the thickness of the glass plate 1 than the upper thickness section 20. Generally, the thickness sections 20, 21 do not extend over the entire thickness of the glass plate 1. E.g., the first 20 and in particular the second thickness section 21 can be predetermined such that after etching in the region of the recess a thickness of the glass plate 1, or between the recess 2 and the second surface 5, of at least 5%, at least 10% or at least 15% or at least 20% remains.

The invention further relates to a method of analysis in which reaction vessels in glass are irradiated with light and light emanating from the reaction vessels is detected, and to the use of the reaction vessels made of glass in the method of analysis.

Therein, light for analysis can preferably be irradiated approximately perpendicularly onto the glass plate, onto the first surface of the glass plate and/or into the open recesses in the glass plate, or onto second the surface of the glass plate lying opposite to its first surface.

It has shown that recesses, in particular recesses which extend conically from the first surface into the volume of the glass plate, upon irradiation with, e.g., visible light form a clear contrast to the bottom of the recesses. Through optical detection, therefore, the circumference of the recesses can be recorded and displayed, in particular as a dark ring in contrast to the bottom of the recesses.

Further, the invention relates to methods for analysis comprising the step of providing reaction vessels which are manufactured according to a production method according to the invention, or which are reaction vessels according to the invention, introducing sample, e.g. a patient sample, which may be cell-free, e.g. blood plasma, or cell-containing, e.g. whole blood or cells separated from whole blood, or tissue material, into reaction vessels, prior to, simultaneously or subsequently, adding at least one reagent into reaction vessels, and analyzing. The reaction vessels produced by the method and the reaction vessels according to the invention have the advantage that the bottoms of the reaction vessels have concave depressions and cells can be arranged singly in concave depressions.

Optionally, the at least one reagent may be added, singly or sequentially multiple times, in different amounts to several reaction vessels. The reagent may be, e.g., an active pharmaceutical agent, and the analyzing may comprise measuring the effect of the active agent on the sample. Optionally, the method may comprise one or more incubation steps, e.g., under cell culture conditions (37° C., 5% $CO_2$ atmosphere, quiescent or with agitation).

Analyzing can be an optical measurement of the reaction vessels, e.g. during or after sequencing of DNA and/or RNA and/or of protein in the reaction vessels after addition of reagents for sequencing, optionally after lysis of cells, or the determination of proteins, e.g. after reaction with a binding molecule added as a reagent, e.g. an antibody, which is preferably labeled with a dye. Preferably, for samples containing cells, e.g., the analyzing comprises determining the transcribed RNAs and/or the translated proteins, in particular for samples to which no active agent was added compared to samples to which active agent was added. Optionally, the method of analysis may comprise removing a portion of the sample from a reaction vessel, further optionally adding the removed sample portion to another reaction vessel according to the invention or produced according to the invention. The addition of sample and/or reagent to the reaction vessels can be performed, e.g., by moving liquid drops of the sample and/or liquid drops of the reagent, wherein the liquid drops are generated and moved, e.g., as part of a liquid jet, e.g. by exposure to electromagnetic irradiation, by application of sound or ultrasound, by application of an electric field, or by application of pressure. The generation of liquid droplets is known as inkjet printing process or pipetting. Alternatively, laser-based printing processes, e.g. laser transfer printing, can be used. Preferably, the addition of sample and/or of reagent is performed without contact of the dosing device with the reaction vessel.

In embodiments in which strip conductors are disposed at the recesses, methods of analysis may involve applying voltage to the interior volume of the recesses and between the strip conductors measuring electrical parameters present in the interior volume.

The figures show schematically in

Figure 2:
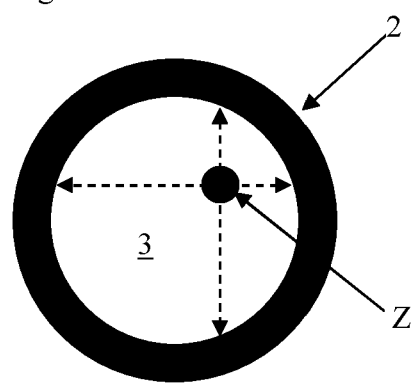

FIG. 1 in cross-section perpendicular to the surface of the first glass plate, an embodiment of the reaction vessels in a single-piece glass plate, FIG. 2, in top view onto the first surface of the glass plate, the optical analysis of a reaction vessel produced according to the invention, and in FIG. 3a), b), c) show further embodiments in cross-section perpendicular to the surface of the first glass plate.

FIG. 1 shows a recess 2 in a first glass plate 1, which can be produced by etching a first glass plate 1 after irradiation with a pulsed laser beam. Therein, the bottom 3 shows concave depressions which have an approximately parabolic cross-section. Such concave depressions are formed at each position 12 at which a laser beam has been irradiated punctiformly. Presently, a bottom 3 having concave depressions is obtained by spot-irradiating laser beams at positions at intervals corresponding to the spacing of the centers of the depressions. Etching, which follows subsequent to the irradiation, removes the areas of the first glass plate 1 between the positions. For this single-piece embodiment, the laser beam irradiated onto the first surface 4 may be set up to penetrate only up to a portion of the volume of the first glass plate 1, and/or the second surface 5 opposite to the first surface 4 may be coated all-over with etch resist.

FIG. 2 in top view onto a glass plate 1 shows a recess 2 the wall of which forms a strong optical contrast with the bottom 3, so that the wall is clearly shown as a circumferential boundary of the bottom 3. A particle, e.g. a biological cell Z, can be seen with clear contrast against the bottom 3 when illuminated through the bottom 3, especially when the cell Z is marked by a dye, e.g. a fluorescent dye.

FIG. 3 shows embodiments of each of a recess 2 produced as a single piece in a glass plate 1. This shows that the irradiation of laser pulses onto the first surface 4 of the glass plate 1 at a plurality of positions spaced apart by, e.g., 1 to 10 μm and therefore forming a location at which exactly one recess 2 is produced by etching. Therein, by etching at each position 12 on the bottom 3 of the recess 2 a respective concave depression may have been produced as a partial recess 2'.

As shown in FIG. 3a), a glass tip 11 projecting perpendicular to the first surface 4 from the bottom 3 into the recess 2 is produced during etching if at least 3 positions 12 at which laser pulses are irradiated are arranged at a greater distance, e.g. at a distance of 20 µm. Therein, each position 12 at which a laser pulse was irradiated results in a concave depression or partial depression 2' in the bottom 3 during etching.

FIG. 3b) shows that laser pulses irradiated at individual positions 13 and penetrating deeper into the thickness of the glass plate 1 during etching form further recesses 14 there, which extend deeper into the glass plate 1 than the depression at other positions 12 where laser pulses were irradiated to a lesser depth into the glass plate 1. The depth of penetration of the laser pulses into the glass plate 1 can be predetermined by adjusting the focus position and/or the strength of the pulse energy of the laser pulses.

FIG. 3c) shows that the irradiation of laser pulses penetrating deeper into the glass plate 1 at positions 13 arranged side by side during etching there forms another recess 14 extending deeper into the thickness of the glass plate 1 than the recess of which bottom 3 is formed during etching from other positions 12 where the laser pulses have been irradiated less deeply into the glass plate 1.

List of reference signs:

1 Glass plate
2 Recess
2' Partial recess
3 ~~Ground~~ Bottom
4 First surface
5 Second surface
7 longitudinal center axis
8 Etch resist
11 Glass tip
12 Position of irradiated laser pulse
13 Position of deeper irradiated laser pulse
14 ~~more~~ Further recess
20 Upper, first thickness section
21 Lower, second thickness section
Z Cell

The invention claimed is:

1. A reaction vessel arrangement, comprising:
a glass plate;
recesses in the glass plate, wherein the recesses do not extend through an entire thickness of the glass;
walls formed by the glass plate separating the recesses from each other, wherein the walls terminate in a common plane with openings of the recesses formed by a first surface of the glass plate;
a pattern of concave depressions at at least 30 positions in a bottom of at least one of the recesses, wherein the depressions comprise a parabolic or conical cross-section, and wherein bottoms of the recesses are formed by material of the glass plate.

2. The reaction vessel arrangement according to claim 1, wherein adjacent recesses form reaction vessels.

3. The reaction vessel arrangement according to claim 1, comprising at least one deeper recess formed in the bottom of the at least one of the recesses, wherein the at least one deeper recess extends a greater depth into the glass plate than the at least one of the recesses.

4. The reaction vessel arrangement according to claim 1, comprising at least one glass tip formed in a single piece from the glass plate in the bottom of the at least one of the recesses, the at least one glass tip being configured as an optical waveguide for near-field illumination of the recess, there the at last one glass tip extends into the the at least one of the recesses perpendicularly to the first surface of the first glass plate.

5. The reaction vessel arrangement according to claim 1, wherein the recesses taper conically or frustroconically.

6. The reaction vessel arrangement according to claim 1, wherein the recesses comprise a depth of at least 30 µm and a depth to diameter aspect ratio of at least 2 of measured in a plane of a first surface of the glass plate.

7. The reaction vessel arrangement according to claim 1, wherein the depressions comprise a depth of 1 to 5 µm.

* * * * *